(12) United States Patent
Castro

(10) Patent No.: US 6,443,919 B1
(45) Date of Patent: Sep. 3, 2002

(54) CUSTOM ANKLE BRACE SYSTEM

(76) Inventor: Ernesto G. Castro, 714 S. Glenview St., Mesa, AZ (US) 85204

( * ) Notice: Subject to any disclaimer, the term of this patent is extended or adjusted under 35 U.S.C. 154(b) by 0 days.

(21) Appl. No.: 09/627,033

(22) Filed: Jul. 27, 2000

Related U.S. Application Data

(62) Division of application No. 08/991,744, filed on Dec. 16, 1997, now Pat. No. 6,155,997.

(51) Int. Cl.$^7$ .................................................. A61F 5/00
(52) U.S. Cl. ............................ 602/27; 602/65; 128/882
(58) Field of Search ................................ 128/846, 882; 602/23, 27, 60, 65

(56) References Cited

U.S. PATENT DOCUMENTS 3,832,780 A * 9/1974 Lewis ........................ 33/2 R
5,687,467 A * 11/1997 Bergmann ................ 29/407.05
6,006,412 A * 12/1999 Bergmann ................ 29/407.05

* cited by examiner

Primary Examiner—Michael A. Brown
(74) Attorney, Agent, or Firm—Martin L. Stoneman

(57) ABSTRACT

A custom ankle brace which is made to compensate for debilitating conditions of an individual patient's ankle area. The brace is custom made by creating a negative cast of the patient's foot/ankle/lower-leg; and then prescribed markings are included on the negative cast by the castmaker to indicate the desired geometry of support. The markings are transferable to a positive cast to inform the bracemaker. The custom brace has inner and outer material layers with a stiffening element within, all fitted to the shape of a built-up positive cast, the stiffening element having a unitary horizontal partial sole portion and vertical back-and-sides-of-leg portion. The stiffening element, made from a thin polymeric sheet, is vacuum and heat fitted to the built-up-positive cast.

17 Claims, 10 Drawing Sheets

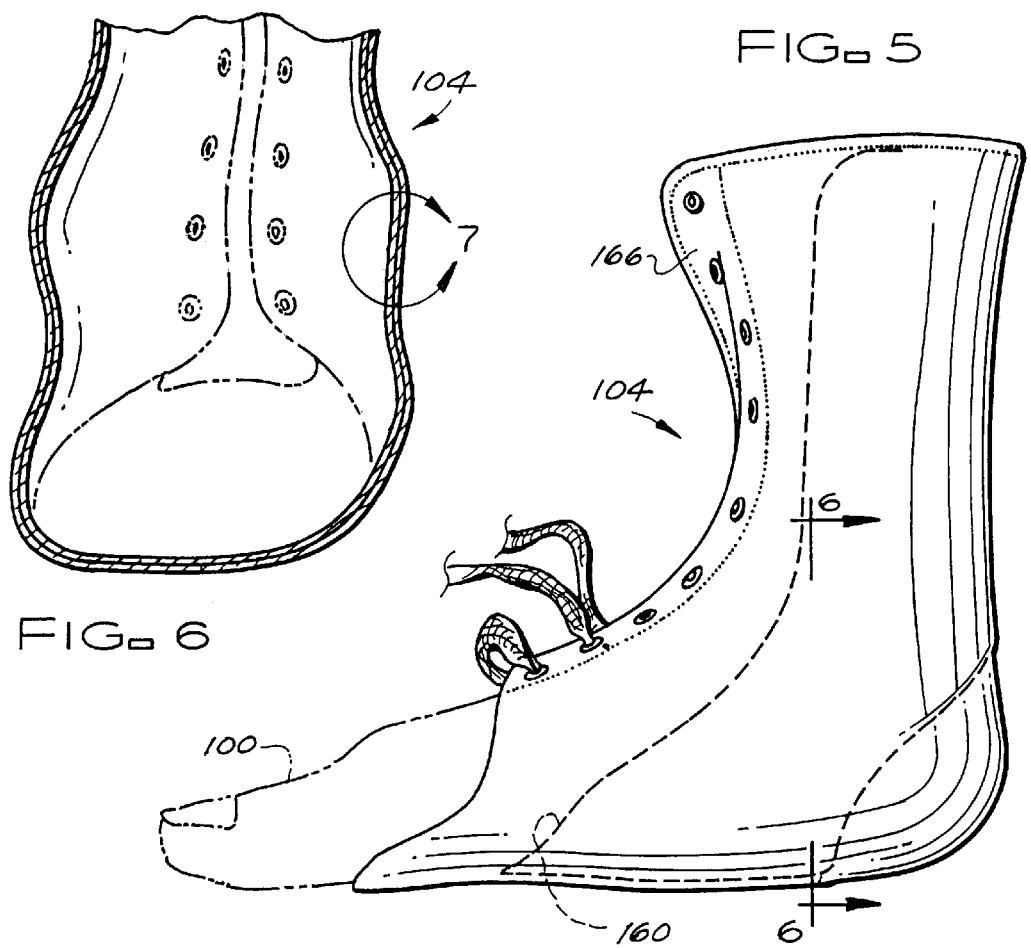
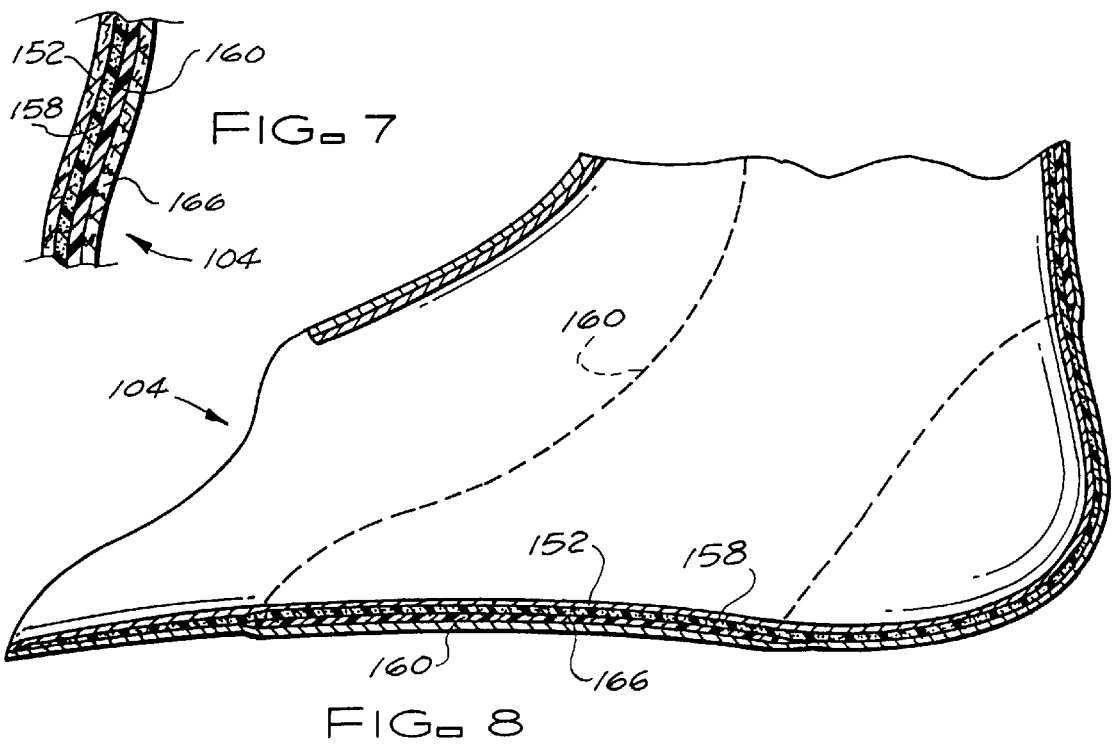

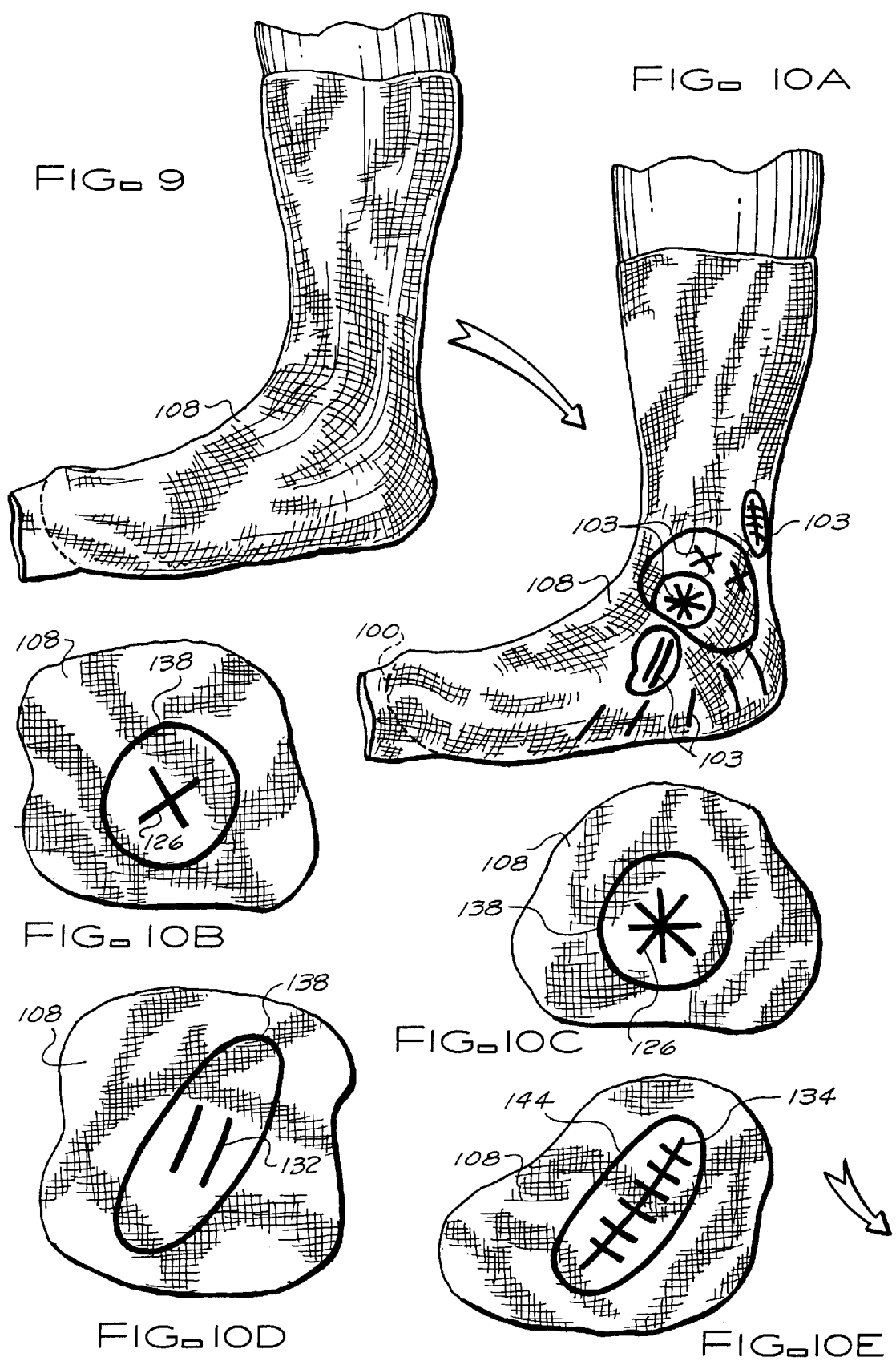

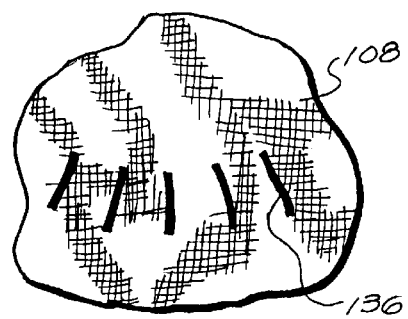
FIG. 10F
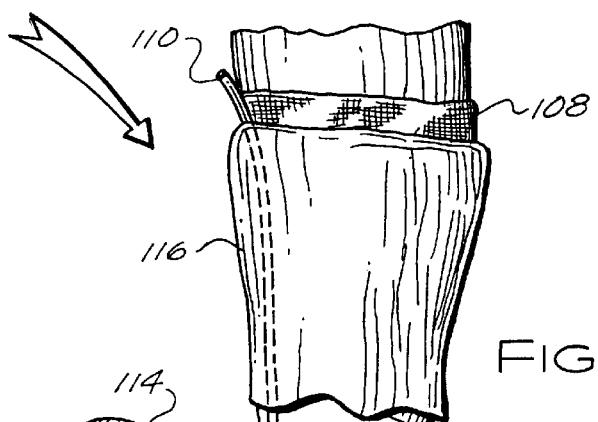
FIG. 11
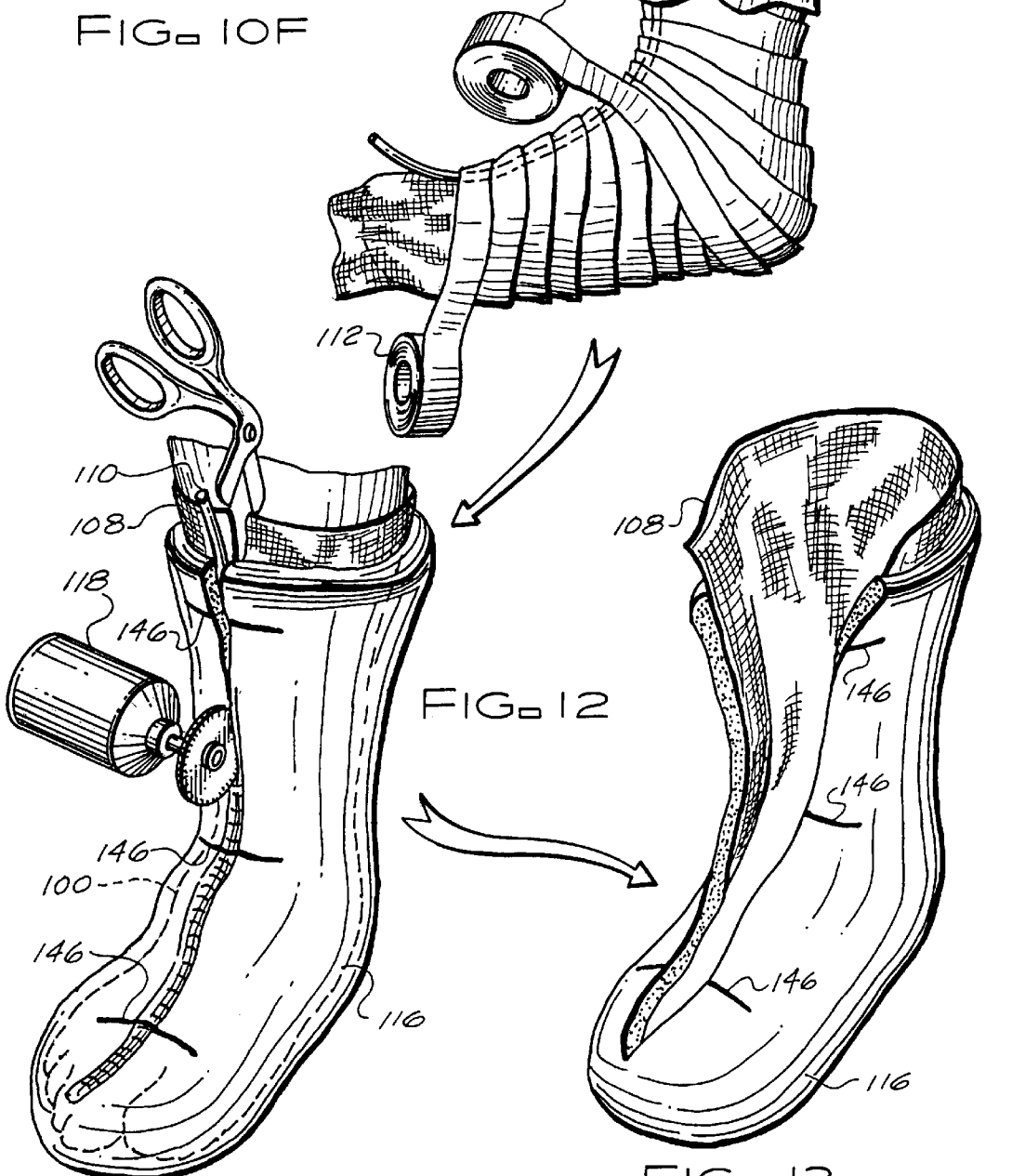
FIG. 12
FIG. 13

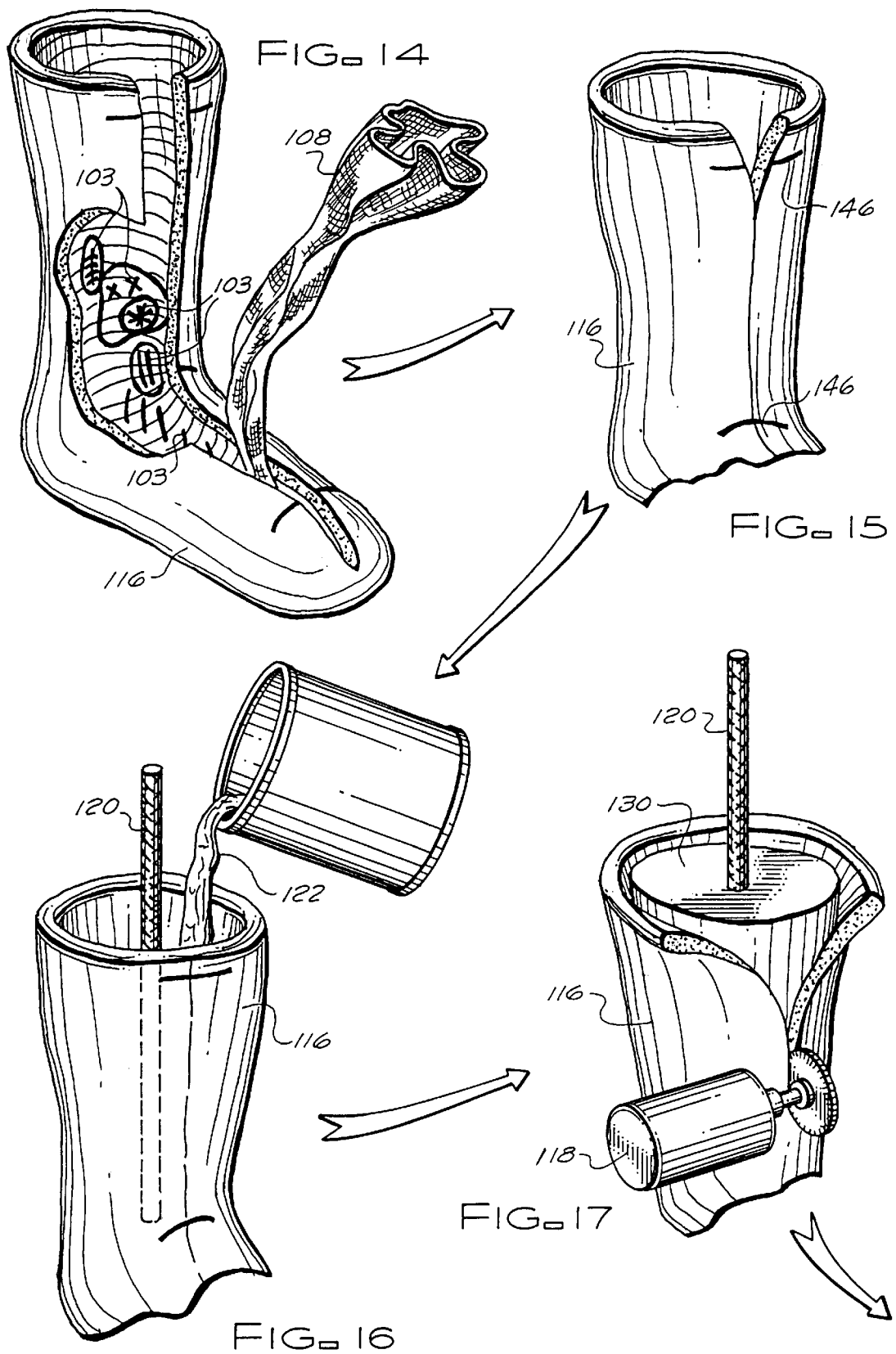

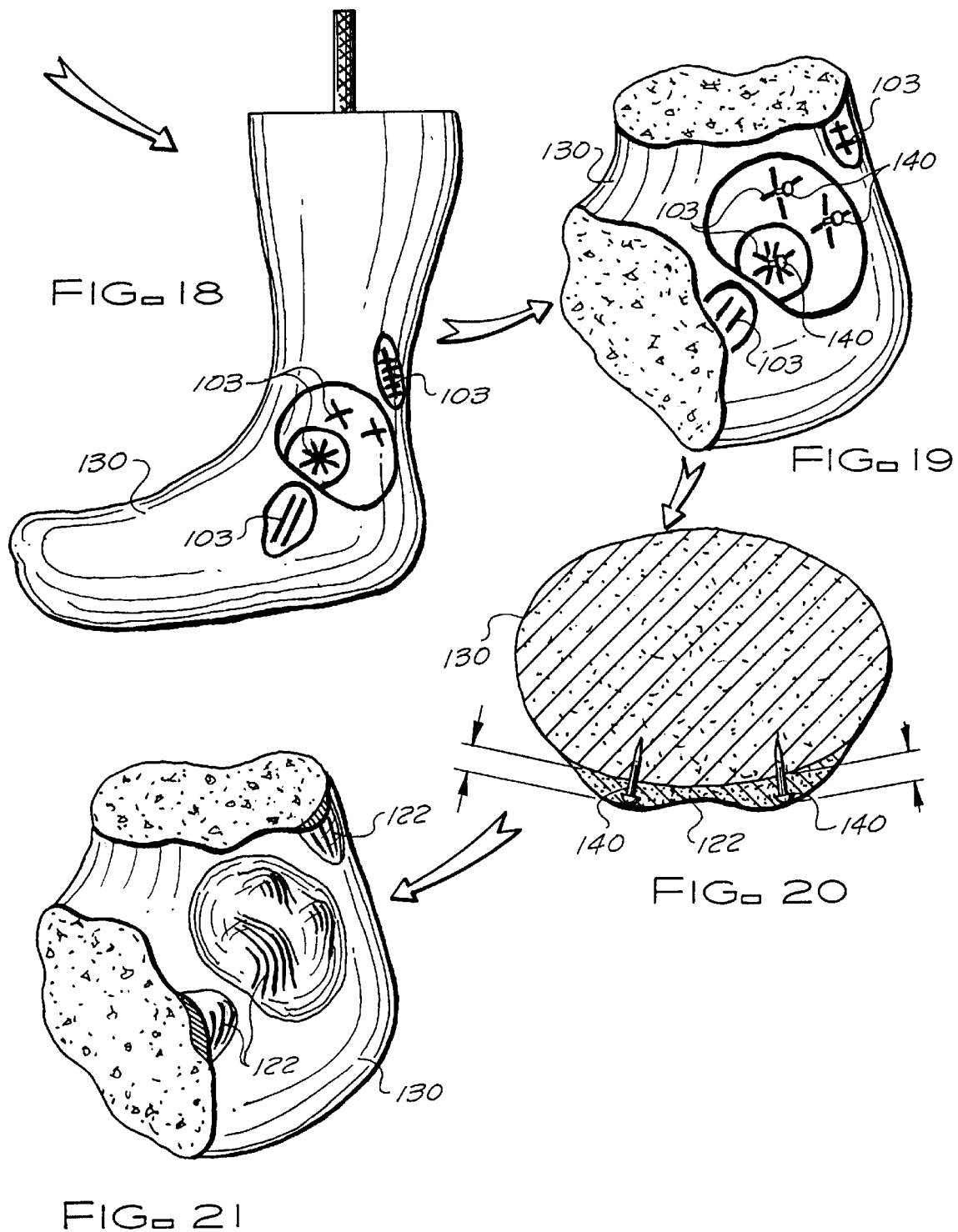

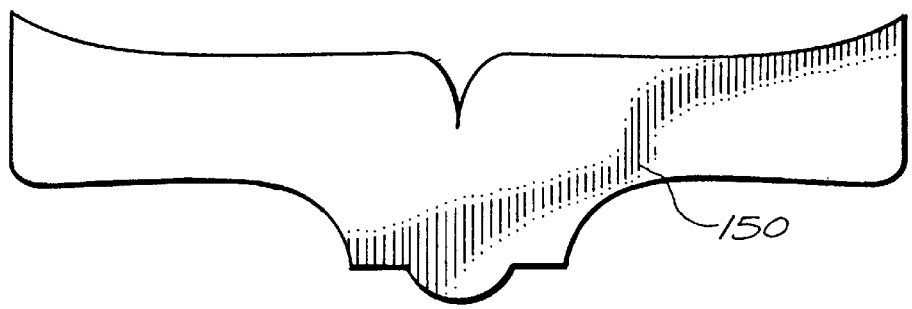
FIG. 22
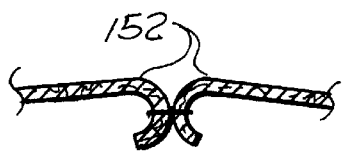
FIG. 23
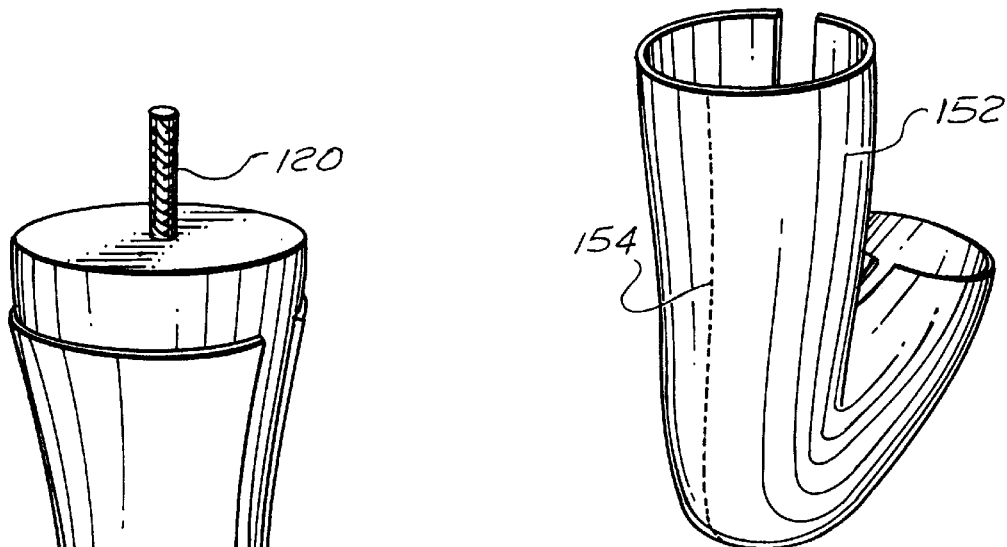
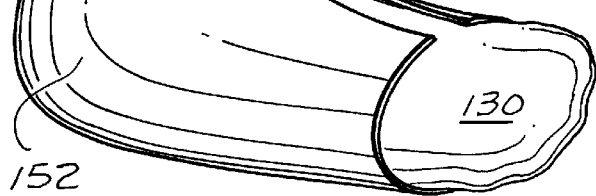
FIG. 24
FIG. 25

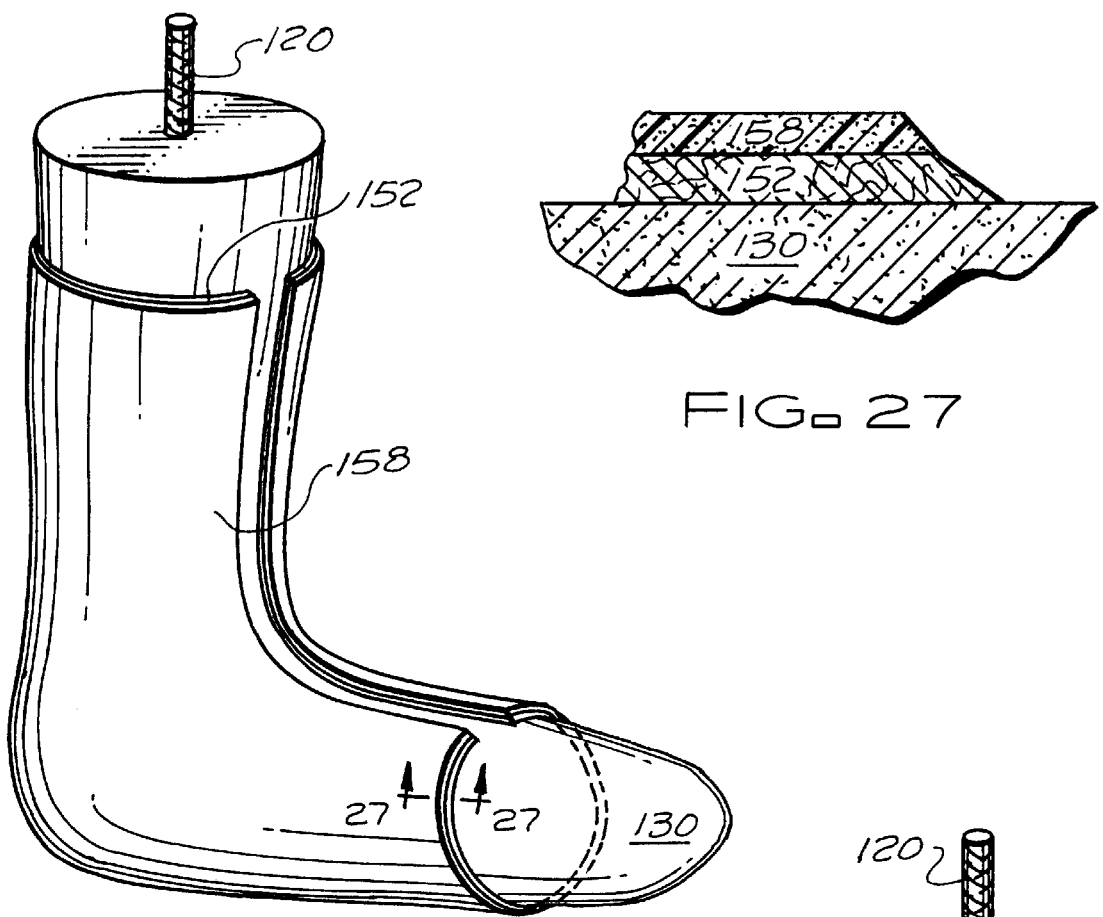
FIG. 26
FIG. 27
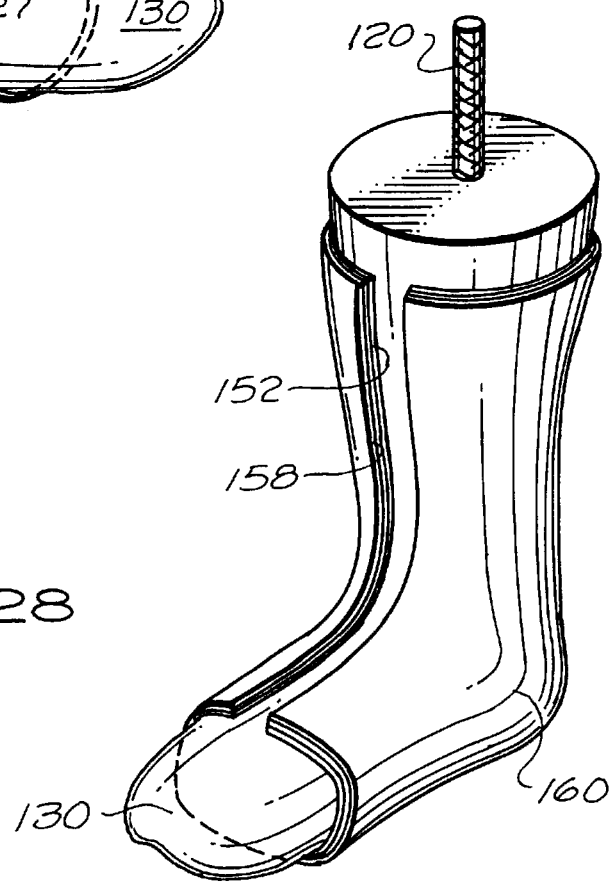
FIG. 28

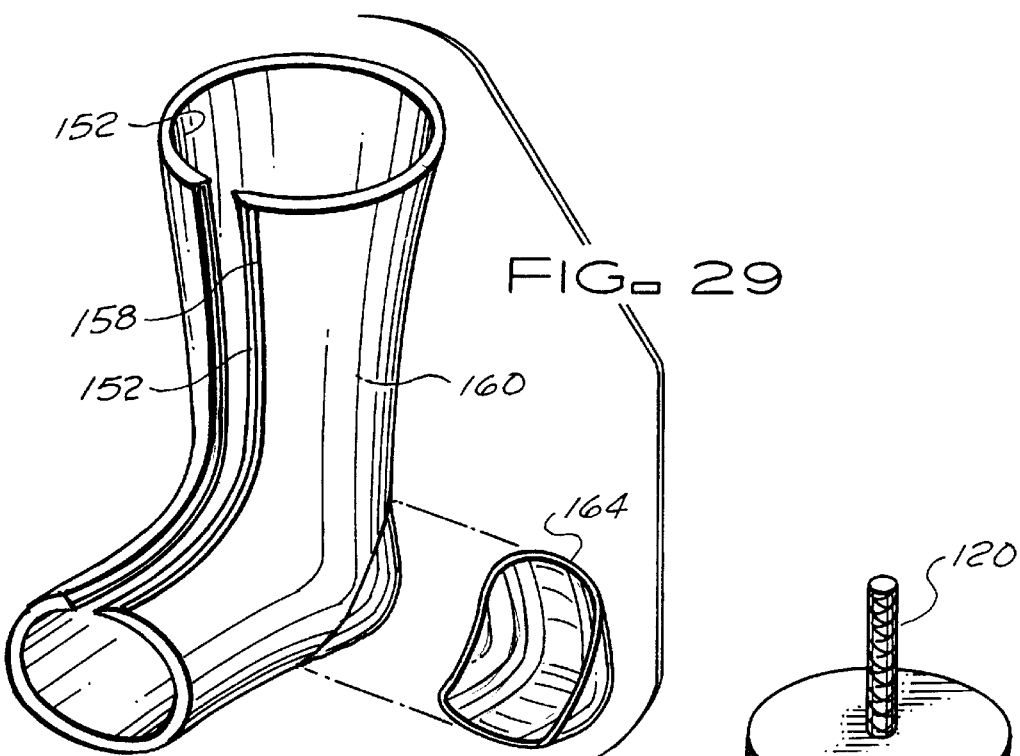
FIG. 29
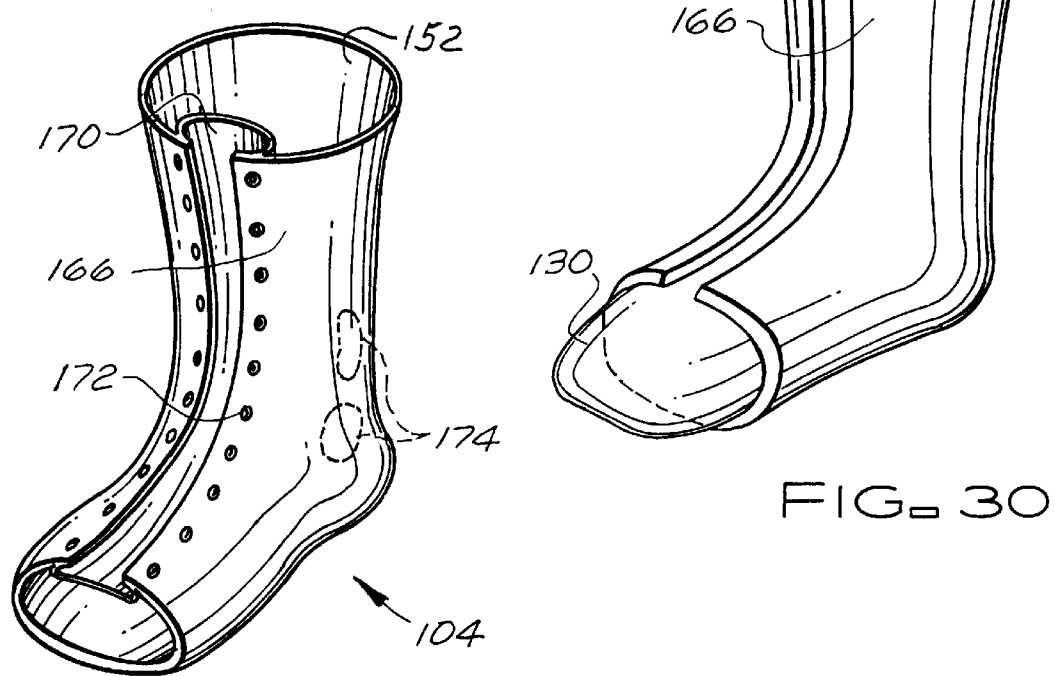
FIG. 30
FIG. 31

CUSTOM ANKLE BRACE SYSTEM

This is a division of application Ser. No. 08/991,744 filed Dec. 16, 1997, now U.S. Pat. No. 6,155,997.

BACKGROUND OF THE INVENTION

1. Field of the Invention

This invention relates to providing a custom ankle brace system. More particularly, this invention concerns such a system for being of help to patients whose ankle conditions are of certain types and no longer permit them to walk properly without some sort of custom orthotic.

2. Description of the Prior Art

Typically, individuals suffer from certain conditions of the feet which either greatly limit unaided mobility or require the use of aids such as walkers or canes in order for the individual to be mobile. Conditions which may cause this debilitating condition include tibialis tendinitis or rupture, degenerate joint disease, talocalcaneal varus or valgus, severe pronation, and/or trauma to ankle, subtalar, or midtarsal. To treat these conditions necessarily requires a stabilizing-type apparatus in order to stabilize the ankle area, talocalcaneal, midtarsal, and subtalar joints so that medial and lateral stability of the foot is achieved with the result that the patient enjoys the benefits of greater mobility.

To compensate for the above stated conditions, a person so afflicted must either compensate for it by purchasing a shoe or shoes that can be many sizes larger than they would normally require, resulting in an awkward appearance and an uncomfortable fit. Furthermore, if the individual has an ailment that affects only one foot, he or she must purchase multiple pairs of shoes in order to get a matching set. One set must be purchased in order to get a shoe that fits the unaffected foot, and the larger matching set to get a shoe that fits the afflicted foot, resulting in a pair of shoes costing at least double what would ordinarily be paid. Alternately, the afflicted individual may try to correct the condition by the use of mechanical devices such as braces which attempt to stabilize the foot so that the heel is more aligned with the bones in the lower leg. Generally, the braces used for these types of ailments are large, thick, and cumbersome, which make them inconvenient to use, awkward in appearance and awkward in fit, and often resulting in sores. Thus there exists a need in treating the above mentioned conditions of the feet for a therapeutic foot brace that overcomes such disadvantages.

OBJECTS OF THE INVENTION

A primary object of the present invention is to fulfill the above-mentioned needs by the provision of a custom ankle brace system overcoming the above-stated problems. A further primary object of the present invention is to provide such an ankle brace system which is efficient and permits the patient to wear essentially normal shoes. In addition, it is a primary object of this invention to provide such a custom ankle brace system in connection with, and making use of, a novel custom ankle brace. Other objects of this invention will become apparent with reference to the following invention descriptions.

SUMMARY OF THE INVENTION

According to a preferred embodiment of the present invention, this invention provides an ankle brace system, for orthotic assistance to an ankle of a patient and adapted to be worn inside a shoe, comprising the steps of: placing a thin flexible stocking-like covering over such ankle of such patient; making markings on such covering on its outside surface to indicate the specific geometry of orthotic support necessary for such ankle, such markings being done in such manner as to be information-transferable to a negative cast overlaying such covering; with the patient's sole placed in about a horizontal plane and lower leg placed vertically, making a negative cast overlaying such covering; removing such negative cast from such ankle of such patient; such markings being selected from a standard identified group knowable to both the castmaker and the bracemaker, and done in such manner as to include marking information at least relating to a preferred geometry of positive cast build-up for use in making an ankle brace for such patient; and removing such covering from inside such negative cast, whereby such markings remain on an inside surface of such negative cast.

Moreover, this invention provides such an ankle brace system further comprising the steps of: making a positive cast from such negative cast in such manner that such markings are information-transferable to an outside surface of such positive cast; whereby such markings remain on such outside surface of such positive cast; and using such marking information, modifying such positive cast in such manner as to make such positive cast build-up for use in making such ankle brace for such patient. It also provides such an ankle brace system wherein such step of modifying such positive cast comprises the steps of: setting nails in such positive cast, the location and geometry of such nails being structured and arranged so that nailheads of such nails conform to such positive cast build-up; applying additional positive cast material to make such positive cast build-up; and smoothening such positive cast build-up.

Furthermore, this invention provides such an ankle brace system further comprising the steps of: using such positive cast, making a support brace pattern having a single vertical seam on the heel side; making material layers to fit such support brace pattern; and making a stiffener element for use within such material layers in making such ankle brace for such patient; wherein such stiffener element is conformable to such positive cast when heated and comprises a partial sole portion and a leg back portion fixed at about a right angle from such partial sole portion. It further provides such an ankle brace system wherein making of such stiffener element comprises the steps of: providing, in a form large enough to enshroud such positive cast, a sheet of polymeric material shapable by vacuum forming when heated; heating such sheet until readily shapable; fully enshrouding such positive cast with such sheet by an air-tight envelopment but for an opening connected to a vacuum source; through such opening, using such vacuum source, creating a negative air pressure within such sheet sufficient to cause such sheet to conform to the shape of such positive cast; maintaining such negative air pressure until such sheet cools sufficiently to stiffen to such shape of such positive cast, thereby providing a shaped element; removing such shaped element from such positive cast; and trimming such shaped element in such manner as to provide such stiffener element.

Additionally, this invention provides such an ankle brace system wherein such making of such stiffener element further comprises the steps of: providing, in a form sufficient to provide extra stiffening to a side of such ankle of such patient opposed to the arch side, a support segment of such polymeric material; heating such support segment until readily shapable; and, between such step of fully enshrouding and such step of creating a negative air pressure, placing such heated support segment into appropriate position on such sheet in such manner as to contact bond to such sheet. And it also provides such an ankle brace system further comprising the step of, using such pattern, making a resilient element for use within such material layers in making such ankle brace for such patient. It further provides such an ankle brace system further comprising the step of, upon such positive cast, assembling some such material layers (after sewing of such single vertical seam) and such stiffener element, thereby providing a partially-made such ankle brace. And it provides such an ankle brace system further comprising the step of providing an arch support in such stiffener element if and as indicated by such marking information.

Even additionally, this invention provides an ankle brace system further comprising the steps of: trimming such partially-made ankle brace according to such marking information for such patient; and applying a such material layer for use as an outer material layer of such ankle brace; and, further, comprising the steps of removing such partially-made ankle brace from such positive cast, and performing final trimming, stitching, and installing of brace closure elements.

Yet further, in accordance with a preferred embodiment thereof, this invention provides an ankle brace system comprising an ankle brace, for providing orthotic assistance to an ankle area of a patient wherein such ankle area includes at least one abnormal protrusion enhancing disability for normal walking, such ankle brace comprising: multiple adhesively-connected material layers forming overall a toe-less boot and shaped to provide room for and support for the abnormal protrusion; and at least one such material layer comprising a stiffener element comprising a partial sole portion lying essentially in a horizontal plane, and an essentially vertical sides-and-back-of-leg portion fixed at about a right angle from such plane of such partial sole portion; such ankle brace being constructed and arranged to be worn by the patient with an essentially normal shoe. And it provides such an ankle brace system wherein at least one of such material layers comprises a foam cushioning material; and, further, wherein such foam cushioning material comprises about a ⅛-inch thick, single density, medical grade polyurethane foam. It also provides such an ankle brace system wherein such stiffener element comprises a polymeric material shapable when heated; and, further, wherein such polymeric material comprises about a 2-millimeter-thick orthopedic grade polymer blend which is auto-adhesive when appropriately heated. And it provides such an ankle brace system wherein the innermost layer of such multiple adhesively-connected material layers comprises a leather material; and, further, wherein such innermost layer comprises 2½ ounce orthopedic tanned leather material. It further provides such an ankle brace system wherein the outermost layer of such multiple adhesively-connected material layers comprises a leather; and, further, wherein such outermost layer comprises a 2½ ounce chromium tanned cowhide leather. And it provides such an ankle brace system wherein such ankle brace further comprises closure elements for tightening and closing such ankle brace on such patient; and, further, wherein such stiffener element does not have a heel portion.

Yet moreover, in accordance with a preferred embodiment thereof, this invention provides an ankle brace system for making, using a positive cast of the foot and lower leg of a patient, an ankle brace, for providing orthotic assistance to an ankle area of a patient, wherein such ankle area includes at least one abnormal protrusion enhancing disability for normal walking, and adapted to be worn inside a shoe, comprising the steps of: making a build-up of such positive cast in the area of such protrusion, sufficient to provide for patient comfort without loss of support; using such positive cast, making a support brace pattern having a single vertical seam on the heel side; making material layers to fit such support brace pattern; and making a stiffener element for use within such material layers in making such ankle brace for such patient; wherein such stiffener element is conformable to such positive cast when heated and comprises a partial sole portion and a leg back portion fixed at about a right angle from such partial sole portion. It also provides such an ankle brace system wherein making of such stiffener element comprises the steps of: providing, in a form large enough to enshroud such positive cast, a sheet of polymeric material shapable by vacuum forming when heated; heating such sheet until readily shapable; placing a talcum-powdered nylon material completely over such positive cast in such manner as to prevent such sheet from sticking to such positive cast; fully enshrouding such positive cast with such sheet by an air-tight envelopment but for an opening connected to a vacuum source; through such opening, using such vacuum source, creating a negative air pressure within such sheet sufficient to cause such sheet to conform to the shape of such positive cast; maintaining such negative air pressure until such sheet cools sufficiently to stiffen to such shape of such positive cast, thereby providing a shaped element; removing such shaped element from such positive cast; and trimming such shaped element in such manner as to provide such stiffener element.

Even additionally, this invention provides such an ankle brace system wherein such making of such stiffener element further comprises the steps of: providing, in a form sufficient to provide extra stiffening to a side of such ankle of such patient opposed to the arch side, a support segment of such polymeric material; heating such support segment until readily shapable; and, between such step of fully enshrouding and such step of creating a negative air pressure, placing such heated support segment into appropriate position on such sheet in such manner as to contact bond to such sheet. It also provides such an ankle brace system further comprising the step of: upon such positive cast, assembling some such material layers (after sewing of such single vertical seam) and such stiffener element, thereby providing a partially-made such ankle brace. And it provides such an ankle brace system wherein such stiffener element is conformed in shape to such positive cast by the application of sufficient heat and pressure to such stiffener element, while such stiffener element is upon such positive cast, to conform the shape of the inside of such stiffener element to the shape of the outside of such positive cast. And it also provides such an ankle brace system further comprising the steps of: removing such partially-made ankle brace from such positive cast; and performing final trimming, stitching, and installing of brace closure elements.

BRIEF DESCRIPTION OF THE DRAWINGS

FIG. 5 is a side elevation view of a preferred embodiment of the custom ankle brace of this invention.

FIG. 6 is a vertical cross-section view through the section 6—6 of FIG. 5.

FIG. 7 is an enlarged cross-sectional view of the area pointed to by the arrows at 7, illustrating the material layers, inner to outer, from left to right in this figure.

FIG. 8 is an enlarged cross-sectional view, showing the material layers, in the aspect of FIG. 5.

FIG. 9 is a side elevation view illustrating the foot and lower leg of a patient upon whom has been placed a thin flexible stocking-like covering.

FIG. 10A is a similar view to FIG. 9 but showing a representative set of markings placed by the user upon the stocking-like covering as indicia explained hereinafter.

FIG. 10B is a close-up view of one representative marking as indicia explained hereinafter.

FIG. 10C is a close-up view of another representative marking as indicia explained hereinafter.

FIG. 10D is a close-up view of yet another representative marking as indicia explained hereinafter.

FIG. 10E is a close-up view of still another representative marking as indicia explained hereinafter.

FIG. 10F is a close-up view of yet still another representative marking as indicia explained hereinafter.

FIG. 11 is a side elevation view illustrating the beginning of the making of a negative cast of the foot and lower leg of a patient, showing particularly the placing of a length of surgical tubing against the center front of the foot and leg to facilitate removal of a plaster cast mold from the illustrated cotton stockinette, and showing the wrapping, first, of elastic plaster bandages are wrapped around the cotton stockinette, followed by a solid plaster bandage, all of the quick-dry typical medical cast plaster.

FIG. 12 is a front perspective view illustrating the removing of the plaster cast negative mold and cotton stockinette from the patient's foot by first cutting the plaster cast along the implanted surgical tubing, as with the illustrated rotary saw, and then cutting the cotton stockinette, as with the illustrated scissors.

FIG. 13 is a front perspective view showing the assembly of FIG. 12 after the there illustrated cutting.

FIG. 14 is a rear perspective view showing the separating and removing of the stockinette from the plaster cast mold, with a cut-away view of the markings transferred to the inside of the plaster cast negative mold from the cotton stockinette.

FIG. 15 is a partial perspective view illustrating the reassembly of the illustrated plaster cast negative mold.

FIG. 16 is a partial perspective view illustrating the insertion into the negative cast of a piece of steel rebar (preferably about ⅜" in diameter) into the center of the negative cast "leg" and the pouring in of plaster cast material.

FIG. 17 is a partial perspective view illustrating the removal of the negative plaster cast mold from the positive plaster cast mold inside, preferably, as Illustrated, with help of a rotary saw.

FIG. 18 is a side view showing that the indelible marks on the negative cast have transferred to the outside of the positive cast, creating a replica of the patient's foot/leg with the markings shown for the additional support, etc.

FIG. 19 is a close-up view, partially in section, showing the markings that have survived transfer from the stockinette to the negative cast and now to the positive cast.

FIG. 20 is a typical horizontal cross-section view in the ankle area of a patient, illustrating the use of small nails (as more particularly hereinafter described) to assist in the buildup of the positive cast at the places and in the manner indicated by the markings, and showing a plaster build up along the markings to a thickness indicated by the small nails installation and the sanding of the cast/mold smooth until it is the desired shape.

FIG. 21 is a close-up view, partially in section, of the ankle area of FIG. 19, illustrating the accomplished build-up areas in accordance with the markings.

FIG. 22 illustrates a representative shape of a paper pattern cut using the positive cast, cutting the pattern so that there is only a single seam at the rear of the pattern (the rear of the ankle).

FIG. 23 is illustrative of the step of sewing the rear seams of the ankle brace, such sewing being a well known art.

FIG. 24 illustrates the inner leather layer in a seam-sewn form.

FIG. 25 illustrates the inner layer placed upon the positive cast for conforming to the cast.

FIG. 26 illustrates the resilient foam layer after placement upon and being adhesively connected to the inner layer, all performed upon the positive cast.

FIG. 27 illustrates a cross-sectional view through the area x of FIG. 26, showing the beveling and feathering of the ends of the inner layer and the foam layer.

FIG. 28 illustrates the polymer stiffening element placed upon the assembled inner and foam layers and conforming to shape of the positive mold (as, for example, by heating), and adhesively connected to the foam layer.

FIG. 29 illustrates the trimming of the polymer stiffening element, including, as illustrated, the usual cutting away of the heel portion of the stiffening element.

FIG. 30 illustrates the leather outer layer placed upon the layers below (including the stiffening element) and adhesively connected to them.

FIG. 31 illustrates the ankle brace removed from the positive cast and undergoing final stitching including having a tongue and eyelets (or other closures) completed (and ready for final fitting to the patient).

DETAILED DESCRIPTION OF A PREFERRED EMBODIMENT AND THE BEST MODE OF PRACTICE

Figure 1:
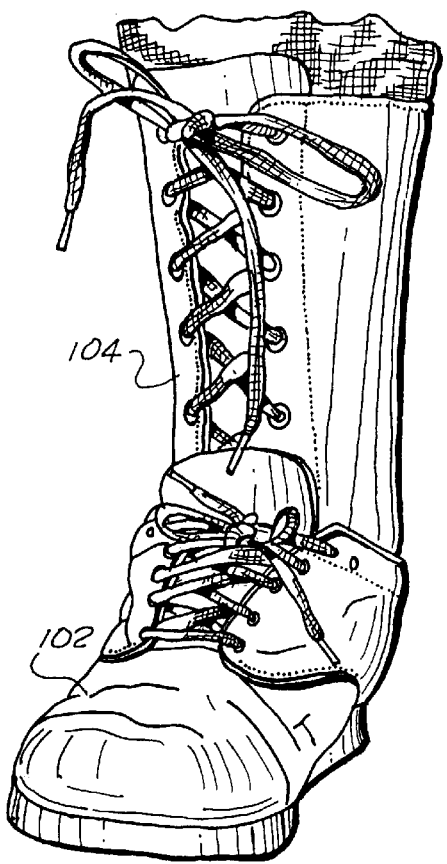
FIG. 1 is a front perspective view of a foot of a patient wearing a custom ankle brace according to the present invention and used by the patient while wearing an essentially normal shoe.
Figure 2:
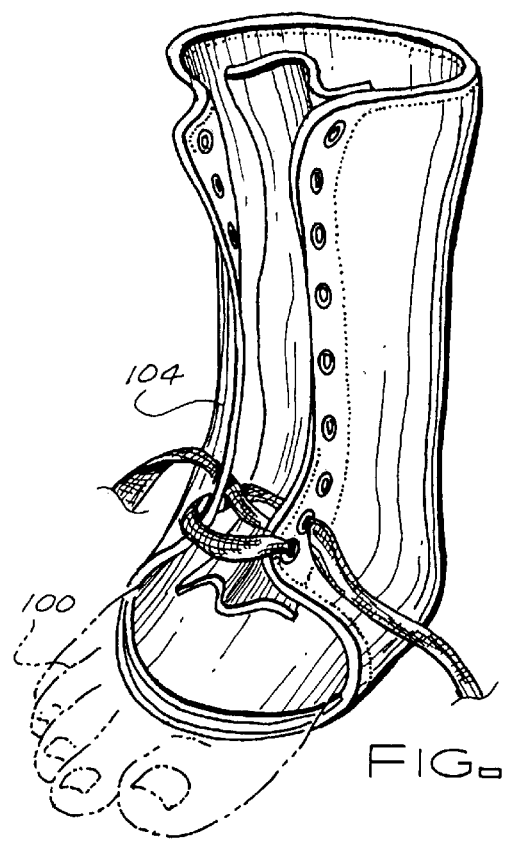
FIG. 2 is a front perspective view of a preferred embodiment of the custom ankle brace of this invention.
Figure 3:
FIG. 3 is a perspective illustration of a foot of a patient, showing a foot with a sensitive bony growth and severe pronation as an example of a typical person who would use the custom ankle brace of the present invention.
Figure 4:
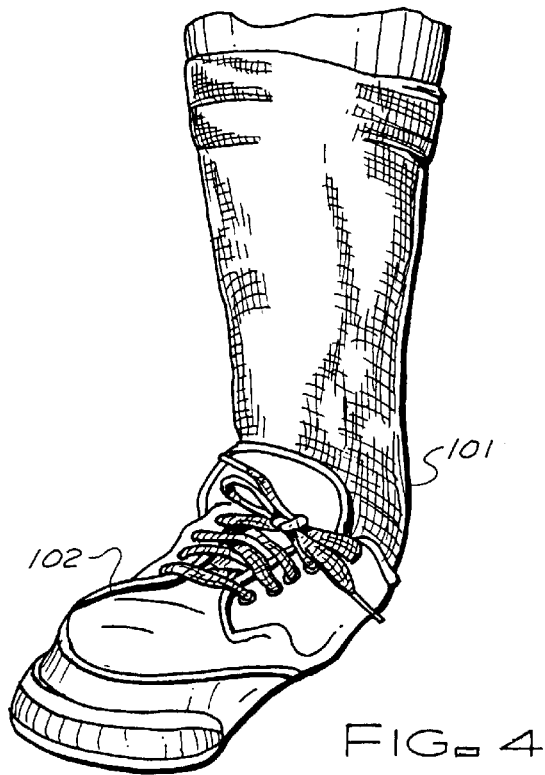
FIG. 4 is a similar perspective view illustrating the problems encountered by a patient with an unsupported foot in conventional footwear.
Figure 32:
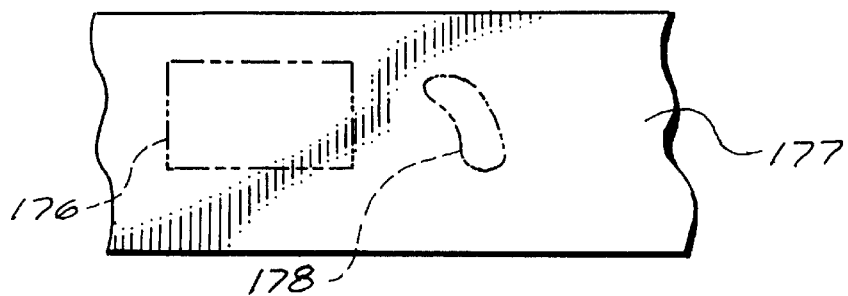
FIG. 32 illustrates the removal of the pieces comprising the stiffening element from a sheet of stiffening element material.
Figure 34:
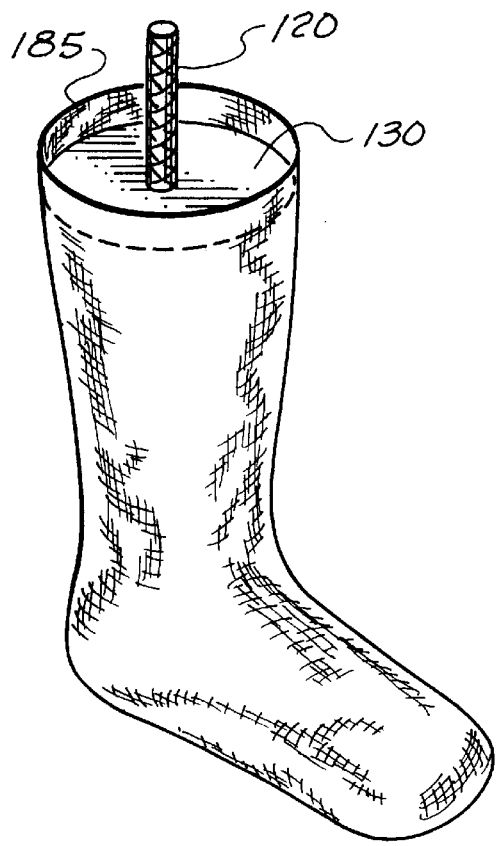
FIG. 34 illustrates the positive cast with a nylon material placed thereon.

FIG. 1 illustrates the custom ankle brace 104 of this invention according to a preferred embodiment thereof. Shown is a shoe 102 worn over the custom ankle brace 104, both holding the patient's foot 100. Typically, the custom ankle brace 104 allows for the patient to wear a shoe size ½ size larger than normal. This is a marked improvement for patients with the type of ailments that the present invention was designed for and it's intended use. Each custom ankle brace 104 is custom manufactured to the specific needs and physical properties of the individual patient's foot 100. FIG. 2 illustrates just the custom ankle brace 104. FIG. 3 represents one possible combination of foot ailments suggesting the use of the custom ankle brace 104. In FIG. 3, a patient's foot 100 is shown with severe pronation and a sensitive bony prominences 101 that would make it difficult for the patient to wear a shoe 102, as illustrated in FIG. 4, and difficult to walk without the use of a brace. Often these patients have had one or more surgeries and may have sensitive scarred areas as well. Generally, the braces used for these types of ailments are large, thick and cumbersome. The patient must purchase a shoe 102 or shoes that are one or many shoe sizes larger than they would normally require. Prior to the initial custom ankle brace 104 manufacturing process, an examination of the patient's foot 100 is performed by a person skilled in the art of said foot ailments and brace-making. A determination of the areas of support that are needed by the patient is made.

FIG. 5 through FIG. 8 more fully illustrate the configuration of custom ankle brace 104 and the layering configuration that is utilized in its construction. Specifically shown in FIG. 5 is the custom ankle brace 104, in elevation, having an outer covering 166 substantially covering a predetermined length of the patients calf, the patient's heel, and a substantial portion of the patient's sole. Also shown in dotted lines in FIG. 5 is a stiffener element 160, hidden from view in this figure, which in the preferred embodiment is a 2 millimeter thick. UCOpoly orthopedic polymer blend. It is used to provide substantially rigid support for the patient's foot 100, and to maintain the patient's sole in a relatively horizontal plane when the lower leg is vertical, thus assisting walking as normally as possible. The various layers comprising the boot 104 are specially made so as to fully conform to the contours of each patients foot, as is more clearly shown in FIG. 6, with said process of making each layer being more fully hereinafter explained. As shown in FIG. 7, with respect to those portions of the boot 104 comprising the stiffener element 160, the boot 104 consists of four individual layers: the leather lining 152, the foam or resilient layer 158, the stiffener element 160, and the outer leather covering 166. The relative location of each of the above layers with respect to the finished boot is more clearly shown in the elevation view of the boot 104 illustrated in FIG. 8. This construction as shown in the figures embodies in this invention multiple adhesively-connected material layers forming overall a toeless boot and shaped to provide room for and support for the abnormal protrusion; and at least one such material layer comprising a stiffener element comprising a partial sole portion lying essentially in a horizontal plane, and an essentially vertical sides-and-back-of-leg portion fixed at about a right angle from such plane of such partial sole portion, such ankle brace being constructed and arranged to be worn by the patient with an essentially normal shoe.

The first step in the custom ankle brace 104 manufacturing process is to make a negative mold plaster casting or negative cast 116 (shown in FIGS. 12–15) of the patient's foot 100. As shown in FIG. 9, a cotton stockinette 108 is placed upon the patient's foot 100, embodying in this invention the step of placing a thin flexible stocking-like covering over such ankle of such patient. FIG. 10A shows the next step in the custom ankle brace 104 manufacturing process which involves marking the cotton stockinette 108 on the previously determined "problem" areas of the foot 100 with markings 103 that will later, e.g., require positive cast build-up for required shaping for reinforcement and/or additional padding, with an indelible type black marker. It is possible several other types or colors of markers might be usable without detracting from the present invention. As will be described in greater detail below, the marks on the cotton stockinette 108 will transfer to the negative cast 116 and then positive cast 130 (see FIG. 18) and eventually will be used by the custom ankle brace 104 manufacturer to build-up the custom ankle brace 104 positive cast 130. This marking step embodies herein the step of making markings on such covering on its outside surface to indicate the specific geometry of orthotic support necessary for such ankle, such markings being done in such manner as to be information-transferable to a negative cast overlaying such covering.

FIGS. 10B, 10C, 10D, 10E, and 10F show possible combinations of these marks as described herein as the best mode of practice. Use of other styles of markings is possible, but it is important that the markings be standard and identified enough so that the castmaker who makes the marks reads them the same way as the bracemaker. FIG. 10B shows a mark used to indicate a bony prominence which will result in a 5 mm (millimeter) build-up on the positive cast 130. This mark, as shown in FIG. 10B, is a solid circle 138 around an X 126; the X 126 marking the apex of the bony prominence. The diameter of the solid circle 138 is determined by the experience and skill of the brace-maker and indicates the area of plaster build up desired on the positive cast 130. FIG. 10C shows a mark used to indicate an extreme bony prominence, which will result in a 10 mm (1 centimeter) plaster build-up on the positive cast 130. This mark, as shown in FIG. 10C, is a solid circle 138 around multiple crossing "X" 126 marks on the extreme bony prominence apex. The diameter of the solid circle 138 is determined by the experience and skill of the brace-maker and indicates the area of plaster build-up desired on the positive cast 130. FIG. 10D shows a mark used to indicate bone that is not prominent but will need a small plaster build-up for additional support, typically 1.5 mm–3 mm on the positive cast 130. This mark is a solid circle 138 around the bone with two parallel lines 132 along the bone. FIG. 10E shows a mark used to indicate painful or sensitive tissue, including scar tissue. An oblong circle 144 is drawn around the sensitive or painful tissue which will result in a 5 mm–10 mm plaster build-up on the positive cast 130. The plaster build-up will allow room for the use of added padding 174, e.g., as shown in FIG. 31, in the painful areas. FIG. 10E also shows scar tissue as marked with a longer straight line and several small shorter lines crossing perpendicular to the longer straight line 134. FIG. 10F shows a mark used to indicate where extra support is needed or wanted as determined by the experience and skill of the brace-maker and indicates the area of plaster build-up that will be added to the positive cast 130. Shown here as an example is the mark used to indicate a flat arch with a needed extra support that will require cutting out of the positive cast 130 in the medial arch and anterior sastitacacum area of the foot. This mark is indicated by several lines 136 parallel to each other along the area of support, the amount to be cut out being directly correlated with the closeness of the markings. The thickness of the plaster built-up on the positive cast 130 is determined by the experience and skill of the brace-maker. This step embodies in this invention the step of such markings being selected from a standard identified group knowable to both the castmaker and the bracemaker, and done in such manner as to include marking information at least relating to a preferred geometry of positive cast build-up for use in making an ankle brace for such patient.

FIG. 11 shows the next step in the custom ankle brace 104 manufacturing process which is a continuation of forming the negative cast 116. With the castmaker making sure that the patient's sole is steady in a horizontal plane and that the patient's lower leg is placed vertically, elastic plaster bandages 112 are wrapped around the cotton stockinette 108 in a manner consistent with the experience and skill of the brace-maker, followed by a more solid plaster bandage 114. The solid plaster bandage 114 is wrapped around the elastic plaster bandage 112 wrap and both wraps cover a small diameter surgical tubing 110 which is preferably used and placed as shown in FIG. 11 along the centerline of the top of the foot 100. This surgical tubing 110 will be used to facilitate removal of the negative cast 116 as shown in FIG. 12. The wet plaster 122 used for this process is standard in the medical industry and known as quick dry medical cast plaster. This step embodies herein the step of, with the patient's sole placed in about a horizontal plane and lower leg placed vertically, making a negative cast overlaying such covering.

In FIG. 12, the next step in the custom ankle brace 104 manufacturing process is shown, which is a continuation of forming the negative cast 116. The negative cast 116 is removed from the patients foot 100. The negative cast 116 is cut off with a plaster cast cutting tool 118, usually a rotary saw of a type well-known by a person skilled in the art. As shown, the cut is made along the surgical tubing 110 previously implanted during the elastic plaster bandage 112 wrap sequence. Before the cut is made, to assist in realigning of the cut line of the negative cast 116 before it used to make a positive cast, alignment marks 146 across the cut line are made.

The next step in the manufacturing of custom ankle brace 104 is a continuation of forming the negative cast 116. And, as shown in FIG. 13, the negative cast 116 is separated; and then, as shown in FIG. 14, the cotton stockinette 108 is removed from the negative cast 116. The cotton stockinette 108 is carefully removed and peeled away from the negative cast 116. When done correctly, the previous markings 103, described above and preferably of the types shown in FIG. 10B through FIG. 10F, will have transferred to the inside of the negative cast 116 as shown in FIG. 14. This step embodies herein the step of removing such covering from inside such negative cast, whereby such markings remain on an inside surface of such negative cast.

FIG. 15 illustrates the next step in the custom ankle brace 104 manufacturing process and final step in the forming of the negative cast 116, the reassembly of the negative cast 116 performed in the usual and well-known manner. The two sides, partially separated during removal from the patient's foot 100, are reassembled by gently urging the cut ends together, making sure the previously marked alignment marks 146 are in alignment.

FIG. 16 shows the next step in the custom ankle brace 104 manufacturing process and the first step in creating a positive cast 130. The inside of the negative cast 116 is coated with a releasing agent, typically a soap solution of a kind well known to those in the art. A ⅜" steel rebar rod 120 is placed in the center of the negative cast 116 as medical quick dry wet plaster 122 casting material is poured into the negative cast 116. This ⅜ steel rebar rod 120 is used to hold the positive cast 130 during various phases in the custom ankle brace 104 manufacturing process. After the wet plaster 122 has set, the negative cast 116 is removed as shown in FIG. 17. The negative cast 116 is cut off with a plaster cutting tool 118. The cut is made along the surgical tubing 110 previously implanted during the elastic plaster bandage 112 wrap sequence and still attached to the negative-cast 116. The indelible markings 103 will have transferred to the exterior of the positive cast 130, creating a replica of the patient's foot 100 with the brace-maker's markings 103 as shown in FIG. 18. This step embodies herein the step of making a positive cast from such negative cast in such manner that such markings are information-transferable to an outside surface of such positive cast, whereby such markings remain on such outside surface of such positive cast.

FIGS. 19–21 illustrate the next steps in the custom ankle brace 104 manufacturing process and the final step in creating a positive cast 130. Specifically illustrated in FIG. 19 is the working of the positive cast 130 by adding small nails 140 where plaster build-up is indicated by the markings 103. These small nails 140 are inserted into the positive cast 130 until the spacing between the top of the small nail 140 head and the positive cast 130 is equal to the amount of plaster build-up (5 millimeter, 10 millimeter, etc.) that will be needed as indicated by the indelible markings 103 previously applied. As shown in FIGS. 20 and 21, additional wet plaster 122 is then applied until it is even with the small nail 140 heads and in conjunction with the areas that will need extra support as determined by the skill of the brace-maker. After the added wet plaster 122 has set the brace-maker will begin the process of sanding the positive cast 130 smooth until it is the correct shape as determined by the experience and skill of the brace-maker. These steps embody herein the steps of using such marking information, modifying such positive cast in such manner as to make such positive cast build-up for use in making such ankle brace for such patient; more particularly wherein such step of modifying such positive cast comprises the steps of setting nails in such positive cast, the location and geometry of such nails being structured and arranged so that nailheads of such nails conform to such positive cast build-up, applying additional positive cast material to make such positive cast build-up, and smoothening such positive cast build-up.

The next step in making the custom ankle brace 104, is cutting a paper pattern 150, shown in FIG. 22, using the positive cast 130. The paper pattern 150 is cut by a person so skilled in the art such that the only seam is at rear of the custom ankle brace 104, as shown by the illustrated example pattern 150. This step embodies herein the step of, using such positive cast, making a support brace pattern having a single vertical seam on the heel side. After the paper pattern 150 is complete, it is used to cut out the custom ankle brace 104 leather lining or inner layer 152, which in the preferred embodiment consists of a soft leather material, preferably a 2½ ounce orthopedic tanned leather material. The inner layer 152 is stitched, as in the example shown in FIG. 23, so that the inner layer 152 contains only one seam 154 located approximately in the posterior of the brace 104 and extending from the patient's heel upward to the top of the custom ankle brace 104 as shown in FIG. 24. The cut inner layer 152 is then formed and molded on the positive cast 130 for proper fit as shown in FIG. 25. [The ⅜ steel rebar rod 120 protruding from the positive cast 130 may be placed in a holding "tube" or vice on the workbench of the brace-maker to facilitate the application of the inner layer 152, and any additional layers, as well as other Work done on the custom ankle brace 104, as required.] The next step is to cut a ⅛ inch single density medical grade polyurethane foam layer or resilient layer 158 to match the previously cut inner layer 152 using the paper pattern 150. FIG. 26 illustrates the process of forming and gluing the resilient layer 158 to the inner layer 152 and forming it around the positive cast 130.

The brace-maker uses a selected contact bond glue to bond the separate layers together. After the glue has set, the resilient layer 158 is beveled at the ends with a buffing wheel to smoothly transition into the inner layer 152 at the perimeter ends as illustrated in FIG. 27. This embodies herein the step of making material layers to fit such support brace pattern.

Figure 33:
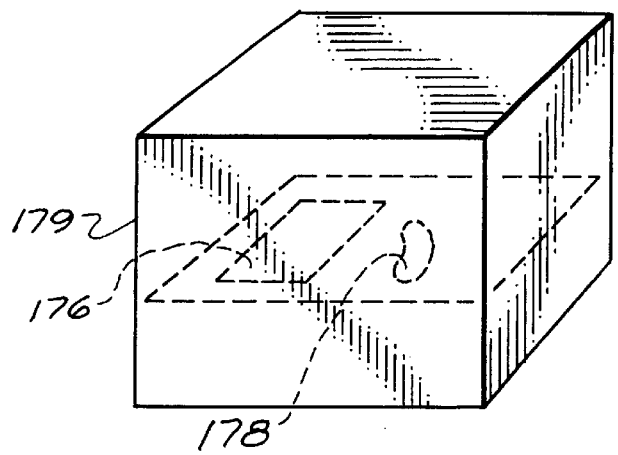
FIG. 33 illustrates the heating step in which the pieces comprising the stiffening element are heated in an oven.
Figure 35:
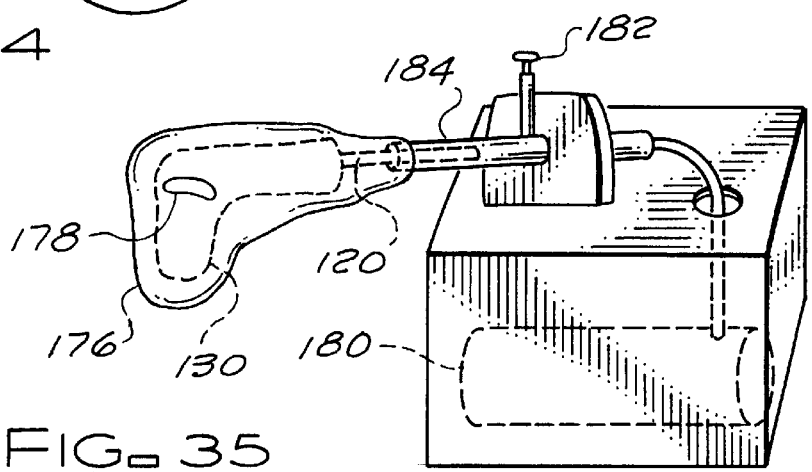
FIG. 35 illustrates the vacuum fitting means to be used in vacuum fitting the stiffening element to the positive cast.

The next step in the construction of the custom ankle brace 104 involves the formation of the stiffener element 160 for use WITHIN such material layers in making such ankle brace for such patient, stiffener element 160 being the main element that is used to provide medial and lateral stability of the foot. It is important that the stiffener element be conformable to such positive cast when heated and that it comprise a partial sole portion and a leg back portion fixed at about a right angle from such partial sole portion (as desired for walking and as illustrated in the figures). As illustrated in FIGS. 32–35, the formation of the stiffener element comprises the steps of cutting a first stiffener piece 176 with dimensions of approximately 16" by 24" from a sheet 177 of heat formable polymer material. In the preferred embodiment, a UCOpoly® orthopedic polymer blend with a thickness of 2 millimeters is used. Next, a second stiffener piece 178 is cut from the same kind of sheet of heat formable polymer material. Such second stiffener piece 178 is be used to provide extra support where needed and has dimensions consistent with providing the needed extra support as determined by the brace maker. Next, the first stiffener piece 176 and the second stiffener piece 178 are heated in an oven 179 to a temperature of approximately 400 degrees Fahrenheit for approximately 3 minutes as illustrated in FIG. 33. Illustrated in FIG. 35 is the vacuum fitting process specifically showing a vacuum fitting means embodied by a vacuum pump and motor 180, a valve 182;, and a suction inlet pipe 184. In applicant's preferred embodiment, a ¼ horsepower motor is used to run the vacuum pump. Prior to attachment of the positive cast 130 to the vacuum fitting means, the positive cast 130 is fitted with a talcum-powdered nylon material or stocking 185 (shown applied in FIG. 34) which is used to prevent the heated first stiffener piece 176 from adhering to the resilient layer 158. The attachment of the positive cast 130 to the vacuum fitting means is accomplished by sliding the ⅜" steel rebar rod 120, extending from the upper end of the positive cast 130, into the end opening of the suction inlet pipe 184. The heated first stiffener piece 176 is then removed from the oven while wearing appropriate gloves and placed fully around the positive cast 130. The free ends of the first stiffener piece 176 are touched together and touched to the suction inlet pipe 184 (near its end opening) thereby forming an air-tight shroud (see FIG. 35) around the positive cast 130. Next, the heated second stiffener piece 178 is placed in the desired position on the first stiffener piece 176, thereby auto-sealing the first stiffener piece 176 and the second stiffener piece 178 together since they are both still hot.

Applicant has found that by creating negative pressure within the sealed first stiffener piece 176, a custom fit stiffener element 160 which more fully matches the contours of the individual patient's feet may be obtained. FIG. 35 illustrates that the negative pressure is obtained by opening valve 182 thereby allowing the vacuum 180 to vacate the air trapped within the shroud of the sealed first stiffener piece 176 so that the first stiffener piece 176 becomes vacuum fitted to the positive cast 130. The negative pressure is maintained until the stiffener element 160 cools to a temperature which will allow physical handling of the stiffener element without altering its physical shape, usually about one minute. These described steps (here and just below) embody in this invention the steps of: providing, in a form large enough to enshroud such positive cast, a sheet of polymeric material shapable by vacuum forming when heated; heating such sheet until readily shapable; fully enshrouding such positive cast with such sheet by an airtight envelopment but for an opening connected to a vacuum source; through such opening, using such vacuum source, creating a negative air pressure within such sheet sufficient to cause such sheet to conform to the shape of such positive cast; maintaining such negative air pressure until such sheet cools sufficiently to stiffen to such shape of such positive cast, thereby providing a shaped element; removing such shaped element from such positive cast; and trimming such shaped element in such manner as to provide such stiffener element. Further embodied herein by such steps are the steps of providing, in a form sufficient to provide extra stiffening to a side of such ankle of such patient opposed to the arch side, a support segment of such polymeric material; heating such support segment until readily shapable; and, between such step of fully enshrouding and such step of creating a negative air pressure, placing such heated support segment into appropriate position on such sheet in such manner as to contact bond to such sheet.

Next, the positive cast 130 encased in the stiffener element 160 is removed from the vacuum fitting means and the stiffener element 160 is marked along a trim line wherein such trim line is located by the brace maker according to the amount and type of support required by the individual patient (as previously indicated by the markings 103 on the positive cast 130). The stiffener element 160 is then removed from the positive cast 130, trimmed along the trim lines which usually preferably includes removal of the heel portion as shown in FIG. 29 for better fit within a normal shoe. Then the trimmed stiffener element 160 is re-attached to the positive cast 130 by contact-bond gluing (preferably an appropriate rubber cement) the stiffener element 160 over the ⅛-inch single density medical grade polyurethane foam (the resilient layer 158) and inner layer 152 as illustrated in FIG. 28.

As stated and as shown on FIG. 29, the next step in the custom ankle brace 104 manufacturing process involves the trimming of the custom ankle brace 104 and specifically the 2 millimeter thick UCOpoly® orthopedic polymer blend comprising the stiffener element 160 to accommodate the specific reinforcements and support required and as indicated by the markings 103 on the positive cast 130 and as discussed herein. In the example shown in FIG. 29, the heel portion 164 is removed to better fit within a normal shoe. Next, all the perimeter edges are beveled and shaped to form a smooth transition to the other layers as determined by the skill and experience of the brace-maker. Additional padding 174 (shown by the hidden lines in FIG. 31) that may be required by the castmaker is also added during this phase of the manufacturing process.

FIG. 30 illustrates the application of the final outer leather covering 166 of the custom ankle brace 104. The paper pattern 150 is used to cut the final outer leather covering 166. The final outer leather covering 166 is cut and sewn with a single seam at the rear 154 (as shown in FIG. 24), and contact bond glued to the lower layers, preferably with a rubber cement. The final outer leather covering 166 is then stitched and sewn to the lower inner layer 152 layer. Leather covering 166 is preferably a 2½ ounce chromium tanned cowhide leather.

FIG. 31 illustrates the last step in the manufacture of the custom ankle brace 104, the attachment of the leather "tongue" 170 piece and the lacing/eyelet grommets 172. Other methods of closure of the custom ankle brace 104 are available, including the use of "Velcro" straps. FIG. 31 shows the lacing/eyelet grommets 172 along the centerline of the foot; however, the placement may be altered to provide a more comfortable fit to the patient when required without detracting from the present invention. The final fitting and adjustments, if needed, will be as determined by the skill and experience of the brace-maker or fitter.

Although applicant has described applicant's preferred embodiments of this invention, it will be understood that the broadest scope of this invention includes such modifications as diverse shapes and sizes and materials. Such scope is limited only by the below claims as read in connection with the above specification.

Further, many other advantages of applicant's invention will be apparent to those skilled in the art from the above descriptions and the below claims.

What is claimed is:

1. A method of making an ankle brace system, for orthotic assistance to an ankle of a patient and adapted to be worn inside a shoe, comprising the steps of:
   a. placing a thin flexible stocking covering over said ankle of said patient;
   b. making markings on said covering on its outside surface to indicate the specific geometry of orthotic support necessary for said ankle, said markings being done in such manner as to be information-transferable to a negative cast overlaying said covering;
   c. with the patient's sole placed in about a horizontal plane and lower leg placed vertically, making a negative cast overlaying said covering;
   d. removing said negative cast from said ankle of said patient;
   e. said markings being
      i. selected from a standard identified group knowable to both the castmaker and the bracemaker, and
      ii. done in such manner as to include marking information at least relating to a preferred geometry of positive cast build-up for use in making an ankle brace for said patient; and
   f. removing said covering from inside said negative cast, whereby said markings remain on an inside surface of said negative cast.

2. A method of making an ankle brace system, according to claim 1 further comprising the steps of:
   a. making a positive cast from said negative cast in such manner that said markings are information-transferable to an outside surface of said positive cast;
   b. whereby said markings remain on said outside surface of said positive cast; and
   c. using said marking information, modifying said positive cast in such manner as to make said positive cast build-up for use in making said ankle brace for said patient.

3. A method of making an ankle brace system, according to claim 2 wherein said step of modifying said positive cast comprises the steps of:
   a. setting nails in said positive cast, the location and geometry of said nails being structured and arranged so that nailheads of said nails conform to said positive cast build-up;
   b. applying additional positive cast material to make said positive cast build-up; and
   c. smoothening said positive cast build-up.

4. A method of making an ankle brace system, according to claim 2 further comprising the steps of:
   a. using said positive cast, making a support brace pattern having a single vertical seam on the heel side;
   b. making material layers to fit said support brace pattern; and
   c. making a stiffener element for use within said material layers in making said ankle brace for said patient;
   d. wherein said stiffener element is conformable to said positive cast when heated and comprises a partial sole portion and a leg back portion fixed at about a right angle from said partial sole portion.

5. A method of making an ankle brace system, according to claim 4 wherein making of said stiffener element comprises the steps of:
   a. providing, in a form large enough to enshroud said positive cast, a sheet of polymeric material shapable by vacuum forming when heated;
   b. heating said sheet until readily shapable;
   c. fully enshrouding said positive cast with said sheet by an air-tight envelopment but for an opening connected to a vacuum source;
   d. through said opening, using said vacuum source, creating a negative air pressure within said sheet sufficient to cause said sheet to conform to the shape of said positive cast;
   e. maintaining said negative air pressure until said sheet cools sufficiently to stiffen to said shape of said positive cast, thereby providing a shaped element;
   f. removing said shaped element from said positive cast; and
   g. trimming said shaped element in such manner as to provide said stiffener element.

6. A method of making an ankle brace system, according to claim 5 wherein said making of said stiffener element further comprises the steps of:
   a. providing, in a form sufficient to provide extra stiffening to a side of said ankle of said patient opposed to the arch side, a support segment of said polymeric material;
   b. heating said support segment until readily shapable; and
   c. between said step of fully enshrouding and said step of creating a negative air pressure, placing said heated support segment into appropriate position on said sheet in such manner as to contact bond to said sheet.

7. A method of making an ankle brace system, according to claim 4 further comprising the step of:
   a. using said pattern, making a resilient element for use within said material layers in making said ankle brace for said patient.

8. A method of making an ankle brace system, according to claim 4 further comprising the step of:
   a. upon said positive cast, assembling some said material layers (after sewing of said single vertical seam) and said stiffener element, thereby providing a partially-made said ankle brace.

9. A method of making an ankle brace system, according to claim 8 further comprising the step of:
   a. providing an arch support in said stiffener element if and as indicated by said marking information.

10. A method of making an ankle brace system, according to claim 8 further comprising the steps of:
    a. trimming said partially-made ankle brace according to said marking information for said patient; and b. applying a said material layer for use as an outer material layer of said ankle brace.

11. A method of making an ankle brace system, according to claim 9 further comprising the step of:
   a. removing said partially-made ankle brace from said positive cast; and
   b. performing final trimming, stitching, and installing of brace closure elements.

12. A method of making an ankle brace system, using a positive cast of the foot and lower leg of a patient, an ankle brace, for providing orthotic assistance to an ankle area of a patient, wherein said ankle area includes at least one abnormal protrusion enhancing disability for normal walking, and adapted to be worn inside a shoe, comprising the steps of:
   a. making a build-up of said positive cast in the area of said protrusion, sufficient to provide for patient comfort without loss of support;
   b. using said positive cast, making a support brace pattern having a single vertical seam on the heel side;
   c. making material layers to fit said support brace pattern; and
   d. making a stiffener element for use within said material layers in making said ankle brace for said patient;
   e. wherein said stiffener element is conformable to said positive cast when heated and comprises a partial sole portion and a leg back portion fixed at about a right angle from said partial sole portion.

13. A method of making an ankle brace system, according to claim 12 wherein making of said stiffener element comprises the steps of:
   a. providing, in a form large enough to enshroud said positive cast, a sheet of polymeric material shapable by vacuum forming when heated;
   b. heating said sheet until readily shapable;
   c. placing a talcum-powdered nylon material completely over said positive cast in such manner as to prevent said sheet from sticking to said positive cast;
   d. fully enshrouding said positive cast with said sheet by an air-tight envelopment but for an opening connected to a vacuum source;
   e. through said opening, using said vacuum source, creating a negative air pressure within said sheet sufficient to cause said sheet to conform to the shape of said positive cast;
   f. maintaining said negative air pressure until said sheet cools sufficiently to stiffen to said shape of said positive cast, thereby providing a shaped element;
   g. removing said shaped element from said positive cast; and
   h. trimming said shaped element in such manner as to provide said stiffener element.

14. A method of making an ankle brace system, according to claim 13 wherein said making of said stiffener element further comprises the steps of:
   a. providing, in a form sufficient to provide extra stiffening to a side of said ankle of said patient opposed to the arch side, a support segment of said polymeric material;
   b. heating said support segment until readily shapable; and
   c. between said step of fully enshrouding and said step of creating a negative air pressure, placing said heated support segment into appropriate position on said sheet in such manner as to contact bond to said sheet.

15. A method of making an ankle brace system, according to claim 12 further comprising the step of:
   a. upon said positive cast, assembling some said material layers (after sewing of said single vertical seam) and said stiffener element, thereby providing a partially-made said ankle brace.

16. A method of making an ankle brace system, according to claim 15 wherein:
   a. said stiffener element is conformed in shape to said positive cast by the application of sufficient heat and pressure to said stiffener element, while said stiffener element is upon said positive cast, to conform the shape of the inside of said stiffener element to the shape of the outside of said positive cast.

17. A method of making an ankle brace system, according to claim 15 further comprising the steps of:
   a. removing said partially-made ankle brace from said positive cast; and
   b. performing final trimming, stitching, and installing of brace closure elements.

* * * * *